(12) United States Patent
Leven et al.

(10) Patent No.: US 12,367,949 B2
(45) Date of Patent: Jul. 22, 2025

(54) MONTE CARLO METHOD FOR THE AUTOMATED AND HIGHLY EFFICIENT CALCULATION OF KINETIC DATA OF CHEMICAL REACTIONS

(71) Applicant: Covestro Deutschland AG, Leverkusen (DE)

(72) Inventors: Matthias Leven, Cologne (DE); Jose Gamez, Cologne (DE); Kunibert Rehm, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 915 days.

(21) Appl. No.: 17/284,548

(22) PCT Filed: Oct. 16, 2019

(86) PCT No.: PCT/EP2019/078115
§ 371 (c)(1),
(2) Date: Apr. 12, 2021

(87) PCT Pub. No.: WO2020/079094
PCT Pub. Date: Apr. 23, 2020

(65) Prior Publication Data
US 2021/0343374 A1   Nov. 4, 2021

(30) Foreign Application Priority Data

Oct. 18, 2018   (EP) ..................................... 18201344

(51) Int. Cl.
*G16C 10/00*   (2019.01)
*G16C 20/10*   (2019.01)

(52) U.S. Cl.
CPC ............. *G16C 10/00* (2019.02); *G16C 20/10* (2019.02)

(58) Field of Classification Search
CPC .................................. G16C 10/00; G16C 20/10
See application file for complete search history.

(56) References Cited

U.S. PATENT DOCUMENTS

| | | | |
|---|---|---|---|
| 2003/0236655 A1 | 12/2003 | Govind et al. | |
| 2015/0142398 A1* | 5/2015 | Miller, III | G16C 10/00 703/2 |
| 2017/0233349 A1* | 8/2017 | Johnson | C07D 233/16 548/348.1 |

FOREIGN PATENT DOCUMENTS

| | | |
|---|---|---|
| CN | 104765918 A | 7/2015 |
| EP | 2352107 A1 | 8/2011 |
| JP | H1125063 A | 1/1999 |
| JP | 2008250392 A | 10/2008 |
| WO | 2018102565 A1 | 6/2018 |

OTHER PUBLICATIONS

James W. McIver Jr. and Andrew Komornicki, Structure of transition states in organic reactions. General theory and an application to the cyclobutene-butadiene isomerization using a semiempirical molecular orbital method, Journal of the American Chemical Society 1972 94 (8), 2625-2633 (Year: 1972).*
Mallikarjun Sharada, Shaama et al. "Automated Transition State Searches without Evaluating the Hessian." Journal of chemical theory and computation 8 12 (2012): 5166-74 (Year: 2012).*
Toulhoat, WO 2009144410, English Translation (Year: 2009).*
Swihart M. T. et al, "Assembling gas-phase reaction mechanisms for high temperature inorganic systems based on quantum chemistry calculations and reaction rate theories", Journal of Physics and Chemistry of Solids; Pergamon Preass; London, vol. 66, Nr. 2-4, pp. 364-371, XP027709615, Feb. 1, 2005.
Martínez-Núnez E., "An automated transition state search usind classical trajectories initialized at multipe minima", Physical Chemistry Chemical Physics, vol. 17, Nr. 22, pp. 14912-14921, XP055601422, May 6, 2015.
Keil F. J., "Complexities in modeling of heterogeneous catalytic reactions", Computer & Mathematics with Applications, Elsevier, vol. 65, Nr. 10, pp. 1674-1697, XP028556589, Jan. 3, 2013.
Kratzer P., "Monte Carlo and kinetic Monte Carlo methods", arxiv.org, Cornell University Library, 201 Olin Library Cornell University Ithaca, XP080320087, Apr. 16, 2009.
Hafner J., "Adsorption and reaction of orgnaic molecules on solid surfaces—ab-initio density functional Investigations", Monatshefte for Chemie—Chemical Monthly; an International Journal of Chemistry, vol. 139, Nr. 4, pp. 373-387, XP019592602, Mar. 14, 2008, Springer-Verlag, AU.
Lin Y. et al, "Reliable Modeling and Optimization for Chemical Engineering Applications: Interval Analysis Approach", Reliable Computing; An international Journal devoted to reliable mathematical Computations based on finite representations and guaranteed accuracy, Kluwer Academic Publishers, vol. 12, Nr. 6, pp. 427-450, XP019453859, Oct. 25, 2006.
Rodríguez A. et al, "tsscds2018: A code for automated discovery of chemical reaction mechanisms and solving the kinetics", Journal of computarional chemistry, vol. 39, Nr. 23, pp. 1922-1930, XP055601919, Sep. 5, 2018.
Diedrich M. K. et al, "Experimental Determination of the Activation Parameters and Stereoselectivities of the Intramolecular Diels-Adler Reactions of 1,3,8-Nonatriene, 1,3,9-Decatriene, and 1,3,10-Undecatriene and Transition State Modeling with the Monte Carlo-Jumping Between Wells/Molecular Dynamics Method", Journal of the American Chemical Society, vol. 119, Nr. 43, pp. 10255-10259, XP055593729, Oct. 1, 1997.
Mercero J. M. et al, "Theoretical methods that help understanding the structure and reactivity of gas phase ions", International Journal of mass spectrometry, Elsevier Science Publishers, vol. 240, Nr. 1, pp. 37-99, XP027705154, Jan. 1, 2005.

(Continued)

*Primary Examiner* — Michael J Dalbo
(74) *Attorney, Agent, or Firm* — The Webb Law Firm

(57) ABSTRACT

The present invention relates to a computer-implemented method for calculating transition states of a chemical reaction, and to a system for data processing comprising means for carrying out the method, to a computer program comprising instructions which cause a computer to execute the method and to the use of the computer program.

10 Claims, No Drawings

(56) References Cited

OTHER PUBLICATIONS

Grebner C. et al, "PathOpt—A global transition state search approach: Outline of algorithm", Journal of Computational Chemistry, vol. 34, Nr. 21, pp. 1810-1818, XP055601427, May 4, 2013.
Jacobson L. D. et al, "Automated Transition State Search and Its Application to Diverse Types of Organic Reactions", Journal of Chemical Theory and Computation: JCTC, vol. 13, Nr. 11, pp. 5780-5797, XP055601412, Oct. 17, 2017.
Lin X-X. et al, "A flexible transition state searching method for atmospheric reaction systems", Chemical Physics, North Holland, NL, vol. 450, pp. 21-31, XP029204426, Feb. 11, 2015.
Salciccioli M. et al, "A review of multiscale modeling of metal-catalyzed reactions: Mechanism development for complexity and emergent behaviour", Chemical Engineering Science, vol. 66, Nr. 19, pp. 4319-4355, XP028264661, May 30, 2011.
Hu, X. et al, "A gradient-directed Monte Carlo method for global optimization in a discrete space: Application to protein sequence design and folding" J. Chem. Phys. Oct. 21, 2009; 131(15): 154117.
International Search Report, PCT/EP2019/078115, date of mailing: Jun. 26, 2020, Authorized officer: Przemyslaw Godzina.
Christensen et al., "Semiempirical Quantum Mechanical Methods for Noncovalent Interactions for Chemical and Biochemical Applications", Chemical Reviews, 2016, pp. 5301-5337, vol. 116.
Stenger et al., "Computational Methods for Chemistry and Physics, and Schrodinger in 3+1", Advances in Quantum Chemistry, 2015, pp. 265-298, vol. 71.
Van Mourik et al., "Density functional theory across chemistry, physics and biology", Philosophical Transactions of the Royal Society A, 2014, pp. 1-5, vol. 72.

* cited by examiner

MONTE CARLO METHOD FOR THE AUTOMATED AND HIGHLY EFFICIENT CALCULATION OF KINETIC DATA OF CHEMICAL REACTIONS

CROSS-REFERENCE TO RELATED APPLICATION

This application is a national stage application under 35 U.S.C. § 371 of PCT/EP2019/078115, filed Oct. 16, 2019, which claims the benefit of European Application No. 18201344.1, filed Oct. 18, 2018, each of which is incorporated herein by reference.

DETAILED DESCRIPTION OF THE INVENTION

The present invention relates to a computer-implemented method of calculating transition states of a chemical reaction, and to a system for data processing comprising means of executing the method, to a computer program comprising commands that cause a computer to perform the method, and to the use of the computer program. The invention also relates to a system, to a method and to a means for the automated and efficient determination of kinetic data of chemical reactions.

During a chemical reaction, the geometry of the atoms involved changes and bonds are broken and new bonds are formed. There is also variation here in the energy of the atoms involved and, during the progression of the chemical reaction, it reaches a state of maximum energy, called the transition state. The transition state is a potential wall or activation barrier that divides the reactants from the products of the chemical reaction. If the activation barrier has been overcome, the product is formed. The energy during a chemical reaction can be represented with the aid of what is called a potential hypersurface which depicts the potential energy of the atoms involved in the reaction as a function of their geometry. The potential hypersurface also reflects states in which no products are formed. The direct reaction pathway in which products are formed, overcoming the transition state, can be shown as a curve in which the distances between the individual atoms of the molecules are plotted against energy. With the aid of quantum-chemical methods and mathematical approximation methods, it is possible to calculate the energy of the geometry of a molecule or a system of multiple molecules, where the function space under consideration here includes the degrees of freedom of the molecule. These methods enable the ascertaining of the geometry at the transition state and allow predictions as to the reaction kinetics of a chemical reaction.

A known method by which the geometry can be ascertained at the transition state is that of Newton-Raphson methods. However, the calculation of transition states with the aid of Newton-Raphson methods has some drawbacks. Firstly, a Newton-Raphson algorithm cannot be applied to any arbitrary starting geometry of a molecule, but only to molecular geometries that already approximate very closely to the geometry of the transition state. This is time-consuming because the approximation of a molecular geometry to the geometry of the transition state is typically effected manually, i.e. bond lengths are manually adjusted on a computer. There are also known methods in which other methods are first used to calculate potential hypersurfaces from which possible saddle points are identified. In these methods too, it is thus first necessary to ascertain a geometry already very closely approximating to the geometry of the transition state. For these reasons, the calculation of transition states with the aid of Newton-Raphson algorithms is particularly time-consuming and costly with current computer technology, especially for molecules having more than 100 atoms. For use of the Newton-Raphson procedures and approximations that build thereon, it is also obligatory to calculate second derivatives of the energy according to the nuclear coordinates of the molecule in question. The calculation intensity of second derivatives is proportional to the square of the size of the molecule and is therefore rate-determining in respect of the calculation of activation energies.

Lin et al. ("A flexible transition state searching method for atmospheric reaction systems", Chemical Physics 450-451, 2015, p. 21-31) disclose a method of studying atmospheric chemical reactions in the gas phase. The method comprises, in a first step, a screening based on Monte Carlo methods of potential hypersurfaces by force-field methods, wherein approximate saddle point-like regions are identified. The observable used in the corresponding Monte Carlo method is the value of an energy function. Building on that, an attempt is made, by means of Newton-Raphson methods, to localize chemical transition states. With the Monte Carlo method disclosed here, it is first necessary to simulate the entire potential hypersurface before any approximate saddle point-like regions can be identified at all. Consequently, it is not possible by this Monte Carlo method to specifically optimize saddle point-like regions. For that reason, no efficient utilization of the computing resources used for localization of the saddle points required is possible. The use of the method disclosed here is limited by current computer technology to small molecules having 7 to 30 atoms. Moreover, mathematically highly simplified methods are used.

E. Martinez-Núñez et al. "An automated transition state search using classical trajectories initialized at multiple minima", Phys Chem Chem Phys, 14 Jun. 2015, 17(22): 14912-21; "tsscds2018: A code for automated discovery of chemical reaction mechanisms and solving the kinetics", J. Comp.Chem., 24 Sep. 2018, 39(23)1922-1930) disclose a method of studying chemical reaction pathways. Potential hypersurfaces of chemical molecules are calculated here by mathematically simplified methods. An attempt is subsequently made to calculate the chemically relevant transition states by standard pseudo-Newton-Raphson methods. Another drawback here is that the entire potential hypersurface must first be calculated, which is time-consuming and requires computer power. Moreover, this method too can be applied only to relatively small molecules.

Jacobson et al. ("Automated Transition State Search and Its Application to Diverse Types of Organic Reactions", J. Chem. Theory Comput. 13, 11, 5780-5797) disclose a method of automated calculation of chemical transition states. Chemical transition states are calculated here from chemical equilibrium states. This procedure requires a separate calculation of chemical equilibrium states before an interpolation of the geometries obtained, by which the transition state is approximated, can be performed. In a further step, based on this approximation, an attempt is then made to calculate a transition state geometry. The establishment of the equilibrium states required entails additional work by the person skilled in the art. The interpolation used in the method disclosed cannot be applied successfully to any desired molecular geometries.

Hu et al. ("A gradient-directed Monte Carlo method for global optimization in a discrete space: Application to protein sequence design and folding" J Chem Phys. 2009 Oct. 21; 131(15): 154117) disclose a method of calculating protein structures. In this method, foldings of protein structures are calculated by means of Monte Carlo methods. To accelerate the convergence of the Monte Carlo procedures, gradients are calculated, which affect the direction and size of deflections of the atom positions. The publication does not suggest any possible use of this method for specific calculation of saddle points.

There is thus a need for a method for the calculation of transition states in which a molecular geometry for a transition state of a chemical reaction can be approximated by a simple method, especially a computer-implemented method. More particularly, there is a need for a method by which transition states can be ascertained without having to calculate a potential hypersurface beforehand. This is done by methods that entail great calculation complexity and are qualitatively less exact. More particularly, the employment of methods that include the calculation of second derivatives of the energy according to the atom coordinates, such as Newton-Raphson or pseudo-Newton-Raphson methods, is to be dispensed with as far as possible. These either give poor success rates in the localizing of transition states or are prohibitive in the resources they expend, particularly for large molecules. In this way, it is possible to reduce the load on resources such as processors and storage media.

The problem addressed by the present invention is that of providing a computer-implemented method in which a geometry of a transition state is calculated by a readily employable, especially computer-implemented, method with the aid of a quantum-chemical method. If at all possible, preference is given to using no quantum-chemical method in which the second derivative of the energy has to be calculated by the nuclear coordinates of the molecule in question in order to be able to calculate the transition state. More particularly, it is to be possible to ascertain a molecular geometry for a transition state of a chemical reaction without calculating the potential hypersurface of the chemical reaction beforehand. More particularly, a computer-implemented method is to be provided for calculation of the transition state of molecules having preferably more than 100 atoms.

This object was achieved by a computer-implemented method of calculating transition states of a chemical reaction, comprising the steps of:

A Generating a Starting Geometry
  A1 providing the three-dimensional representation of at least one molecule at ground state energy,
  A2 selecting at least one bond of the at least one molecule and selecting a length of the bond, where the selected length does not correspond to the length of the bond at ground state energy of the molecule, such that a starting geometry for the chemical reaction is obtained,
  A3 representing the starting geometry in three dimensions in Cartesian and/or internal coordinates,
B Ascertaining an Optimized Starting Geometry
  B1 defining a function space encompassing the at least one bond from step A2 and the atoms joined by this bond,
  B2 optimizing the geometry of the function space selected in step B1 by means of a quantum-chemical method and with the boundary condition that the length of the at least one bond selected in step A2 is kept constant, such that an optimized starting geometry is obtained,
  B3 ascertaining the gradient norm B3 for the optimized starting geometry, where the gradient norm is obtained via the first derivative of a function E=f(x) of the quantum-chemical method and, with E=total energy of the optimized starting geometry and x=nuclear coordinates of the molecule in the optimized starting geometry,
  B4.1 when the gradient norm B3 $\nabla$ is $0 \leq \nabla \leq 0.03$ $E_h$ $a_0^{-1}$, classifying the optimized starting geometry as a precursor to the transition state of the chemical reaction and continuing the method with step D1, or
  B4.2 when the gradient norm B3 $\nabla$ is $>0.03$ $E_h$ $a_0^{-1}$, ascertaining the precursor to the transition state of the chemical reaction proceeding from the optimized starting geometry by a method comprising the following steps:
C Ascertaining the Precursor to the Transition State of the Chemical Reaction
  C1 varying the optimized starting geometry using a Monte Carlo algorithm, wherein
  C1.1 at least one atom from the function space selected in step B1 is selected at random,
  C1.2 a vector for a deflection of the atom chosen in step C1 is selected at random, weighting the randomly chosen magnitude of the vector by the gradient norm B3,
  C1.3 the atom selected step C1.1 is deflected from the position of the atom in the optimized starting geometry using the vector from step C1.2, so as to obtain a precursor to a transition state of the chemical reaction,
  C2 optimizing the geometry of the precursor to the transition state by means of the quantum-chemical method and with the boundary condition that the at least one bond from step A2 has the length that was ascertained in step C3,
  C3 ascertaining the gradient norm C3 for the precursor to the transition state from step
  C2, where the gradient norm is obtained via the first derivative of the function E=f(x) of the quantum-chemical method and, with E=total energy of the precursor to the transition state and x=nuclear coordinates of the molecule in the precursor to the transition state,
  C4.1 when the gradient norm C3 $\nabla$ is $0 \leq \nabla \leq 0.03$ $E_h$ $a_0^{-1}$, continuing the method with step D1, or
  C4.2 when the gradient norm C3$\nabla > 0.03$ $E_h$ $a_0^{-1}$ $E_h$ $a_0^{-1}$, repeating steps C1 to C3 until a gradient norm C3 $\nabla$ of $0 \leq \nabla \leq 0.03$ $E_h$ $a_0^{-1}$ is obtained, wherein
    (a) if steps C1 to C3 have been performed once, the geometry of the precursor to the transition state is varied in step C1 when the value of its gradient norm C3 is lower than the value of the gradient norm B3 of the optimized starting geometry, or
    (b) if steps C1 to C3 have been performed more than once, the geometry of the optimized starting geometry or that precursor to the transition state from the preceding repetitions that has the lowest value for the gradient norm C3 or B3 compared to all the gradient norms C3 and B3 previously obtained is varied in step C1,
D Ascertaining the Transition State
  D1 varying the precursor from step C4.1 or the precursor from step B4.1 by performing the following steps for one atom within the function space defined in B1:
  D1.1 selecting an atom from the function space selected in step B1,
  D1.2 selecting a vector for a deflection of the atom chosen in step D1.1,
  D1.3 deflecting the atom selected in step D1.1 using the vector from step D1.2 from its position in the precursor, wherein the position is deflected once by the positive value of the magnitude of the vector and once by the negative value of the magnitude of the vector, such that two deflected precursors are obtained when steps D1.1 to D1.3 are conducted, D2 optimizing the geometry of the two deflected precursors from step D1 by means of the quantum-chemical method under the constraint that the bond distances obtained in D1 are kept constant, such that two optimized precursors (i) and (ii) are obtained, D3 calculating the energy of the two optimized precursors (i) and (ii) from step D2 by means of the quantum-chemical method, D4 comparing the energy values of the two optimized precursors with the value of the gradient norm C3 or B3 of the precursor that was used in step D1, D4.1. if the energy value of the optimized precursor (i) and the energy value of the optimized precursor (ii) are each smaller than the energy value C3 or B3 of the precursor that was used in step D1, classifying the precursor that was used in step D1 as the transition state, D4.2. if the energy value of the optimized precursor (i) or the energy value of the optimized precursor (ii) is not smaller than the energy value C3 or B3 of the precursor that was used in step D1, repeating the method from step C1.

It has been found that, surprisingly, the object can be achieved by using a suitable Monte Carlo method to vary different molecular geometries and approximating a geometry for a transition state with the aid of a quality criterion. Furthermore, it has been found that, surprisingly, the object can be achieved by using the gradient of the curve of the direct reaction pathway as an observable in the Monte Carlo method. This allows the function space under consideration, which is to reflect the molecular geometry at the transition state of the chemical reaction, to be reduced to such a degree that the calculation of saddle points is enabled without calculating a potential hypersurface or manually searching for molecular geometries beforehand. Moreover, it has been found that, surprisingly, the method according to the invention enables the calculation of saddle points in function spaces with a high number of dimensions without using Newton-Raphson-based methods. Rather than the calculation of second derivatives of the energy by the nuclear coordinates, the region around the saddle point is verified by infinitesimal deflections and subsequent geometry optimization. The deflection here along the bond dissociation must result in a decrease in total energy. In this way, it is possible to completely avoid the demanding calculation of the second derivatives of the energy by the nuclear coordinates, as in Newton-Raphson-based methods. With current computer technology, it is possible by the method of the invention to calculate even transition states for molecules having more than 100 atoms in a much shorter and quicker manner, in particular also by the reduction in labour involved in the implementation of corresponding conventional processes. This also saves computer resources.

In step A of the method according to the invention, a starting geometry is first produced by, in step A1, providing the three-dimensional representation of at least one molecule at ground state energy. Then, in step A2, a bond of the molecule is selected, and a length of the bond that differs from the length of the bond at ground state energy, such that a starting geometry is obtained. The selected bonds are preferably those bonds that are formed or broken in the chemical reaction in question. The bond length, which differs from the length of the bond in the energetic ground state, is 10% to 90%, preferably 20% to 40%, greater than the bond in the energetic ground state.

Preferably, the at least one molecule from step A1 has a size of more than 100 atoms, further preferably of more than 80 atoms, more preferably of more than 60 atoms, and/or the length of the bond selected in step A2 is not more than 230 pm, preferably not more than 200 pm, further preferably not more than 180 pm, more preferably not more than 150 pm.

Preferably, step A is executed by a user, who inputs the three-dimensional representation of a molecule in the energetic ground state in step A1, and the selection of a bond and the length of the bond in step A2, and the representation of the starting geometry in step A3, into an input screen for the computer-implemented method.

In a further preferred embodiment of the method according to the invention, in step A1, at least two molecules I and II are provided and, in step A2, alternatively or additionally to the at least one bond, at least one distance between at least one atom from molecule I and at least one atom from molecule II and the length of the at least one distance may also be selected, where the length of the distance is especially not more than 230 pm, preferably not more than 200 pm, further preferably not more than 180 pm, more preferably not more than 150 pm. When the method is performed with at least two molecules I and II and the length of the distance between atoms of the different molecules is selected, the transition state of a synthesis reaction can preferably be calculated by the method. Preferably, molecule I has a size of 2 to 1000 atoms and molecule II a size of 2 to 1000 atoms; more preferably, molecule I has a size of 2 to 800 atoms and molecule II a size of 2 to 800 atoms; even more preferably, molecule I has a size of 2 to 600 atoms and molecule II a size of 2 to 600 atoms. Preferably, the sum total of the atoms from molecule I and from molecule II is more than 100 atoms.

Preferably, molecule I is a catalyst for the chemical reaction, especially for a polymer synthesis, and molecule II is a reactant in the chemical reaction. The polymer synthesis in this embodiment is preferably polyurethane syntheses. The chemical reaction in this embodiment is preferably also syntheses of monomers for polymerization reactions, industrially required commodity chemicals, additives, surfactants and active pharmacological ingredients. In particular, the chemical reaction is a synthesis for commodity chemicals or reactants for chemical syntheses that are obtained with catalysts. Additives are generally understood to mean additives for plastics such as plasticizers, antioxidants, modifiers, and additives for fuels, in the synthesis of which catalysts are used in each case.

In step A3, the starting geometry selected in step A2 is represented in Cartesian and/or internal coordinates. Internal coordinates describe the spatial arrangement of the atoms relative to one another using bond lengths, bond angles and torsion angles.

In step B of the method according to the invention, an optimized starting geometry is ascertained. For this purpose, first of all, a function space is defined in step B1. The function space includes the spatial coordinates of selected atoms, where the spatial coordinates in the vector space of all atom coordinates included in the molecule define a subspace. The selected atoms for the function space are a set of atoms that are involved in a bond dissociation or preferably in a synthesis reaction. In addition, the function space includes the at least one bond from step A2. In the preferred embodiment with at least two molecules I and II, the function space includes the distance between at least one atom from molecule I and at least one atom from molecule II.

In the subsequent step B2, the starting geometry is subjected to a geometry optimization by means of a quantum-chemical method with the boundary condition that the length of the at least one bond selected in step A2 is kept constant, such that an optimized starting geometry is obtained. This geometry optimization includes all the atoms of the molecule selected as starting geometry. In the preferred embodiment with at least two molecules I and II, in the geometry optimization, the distance between at least one atom from molecule I and at least one atom from molecule II is kept constant, such that an optimized starting geometry is obtained. In the geometry optimization with a boundary condition, the total energy of the molecule is minimized as a function of the nuclear coordinates of the atoms present in the molecule by a quantum-chemical method. In order to obtain a local energy minimum, the energy is minimized by gradients (e.g. steepest descent), with minimization of the energy to such an extent as permitted by the boundary condition.

In step B3, the gradient norm B3 is ascertained for the optimized starting geometry obtained beforehand, where the gradient norm is obtained via the first derivative of a function E=f(x) by means of the quantum-chemical method, with E=total energy of the optimized starting geometry and x=nuclear coordinates of the molecule in the optimized starting geometry. In step B3, the same quantum-chemical method is used as in step B2. The Euclidean norm of this vector is the gradient norm. In other words, the gradient vector of the energy is calculated. The gradient vector defines the same vectorial space as the molecule. Each component of the vector consists of the partial derivative of the energy in the $x_i$ coordinates $$\left(\frac{\partial}{\partial x_i} E(x)\right)$$

and extends in the direction of the unit vector of the $x_i$ coordinates. Thereafter, the (Euclidean) norm of this vector is ascertained.

The further continuation of the method on the size of the gradient norm B3 obtained. If the gradient norm B3 $\nabla$ is $0 \leq \nabla \leq 0.03$ $E_h$ $a_0^{-1}$, the optimized starting geometry can be classified as a precursor to the transition state of the chemical reaction and step C of the method omitted and the method continued with step D1. If the gradient norm B3 $\nabla$ is $>0.03$ $E_h$ $a_0^{-1}$, step C of the method is performed and a precursor to the transition state of the chemical reaction is first ascertained, proceeding from the optimized starting geometry. $E_h$ here represents the Hartree energy, where 1 $E_h$=4.3597·10$^{-18}$ J, and $a_0$ represents the Bohr radius, where 1 $a_0$=5.29·10$^{-11}$ m.

In step C, the precursor to the transition state of the chemical reaction is ascertained. For this purpose, the optimized starting geometry is varied using a Monte Carlo algorithm by implementing randomly generated deflections of atoms in an ensemble consisting of one molecule or preferably a geometry of at least two molecules I and II.

Monte Carlo algorithms or methods are simulation methods that analytically solve mathematical problems that are solvable only with difficulty, if at all, by numerical approximations. This is done by describing a most likely progression of an experiment by a multitude of randomly arranged individual experiments.

In the Monte Carlo algorithm according to the invention which is employed in step C, randomly generated deflections of atoms in an ensemble consisting of a molecule or a geometry of at least two molecules I and II are implemented and the change in an observable is observed. This observable is a gradient norm. The method according to the invention here varies only a subspace of distinctly smaller dimensions than the entire function space of the ensemble and considers the change in the observable in the overall ensemble as a function of the reduced function space.

For this purpose, at least one atom is selected in step C1.1 from the function space selected in step B1. This is done with the aid of a random number Z1. The direction of a deflection of the atom chosen by Z1, or the direction of the vector for the deflection, is selected in step C1.2 by a further random number Z2. The direction is preferably defined in that, in the preferred step C1.2a, the position of an atom other than that selected in step C1.1 is selected from the reduced function space and then, in the preferred step C1.2b, the direction of the deflection is selected, where the position of the atom selected in step C1.2a determines the direction of the vector. The amplitude of the deflection is preferably determined via a third random number Z3 in the preferred step C1.2c.

In a preferred embodiment of the method according to the invention, step C1.2 comprises the further following steps of:
C1.2a determining a further atom from the function space selected in step B1 which does not correspond to the atom selected in step C1.1,
C1.2b selecting the direction of the vector, where the position of the atom selected in step C1.2.a determines the direction of the vector,
C1.2.c randomly selecting the length of the vector, where the value of the length of the vector may assume positive or negative values.

The weighting of the randomly selected magnitude of the vector in step C1.2 is preferably effected by multiplying the numerical value of the randomly selected magnitude of the vector by the numerical value of the gradient norm B3.

By virtue of the position of the atom selected in step C1.2 determining the direction of the vector, the function space is restricted as far as possible, and this course of action also has the effect that primarily bond lengths having lengths as are very probably actually achieved during a reaction are varied.

In step C1.3, the atom selected in step C.1.1 is deflected from its position in the optimized starting geometry using the vector from step C1.2, so as to obtain a precursor to the transition state of the chemical reaction.

The precursor to the transition state obtained is subjected to a geometry optimization in step C2 by means of the quantum-chemical method and with the boundary condition that the at least one bond from step A2 has the length that was ascertained in step C1.3. In step C2, the same quantum-chemical method is used as in steps B2 and B3. Then, in step C3, the gradient norm C3 for the precursor to the transition state from step C2 is ascertained, where the gradient norm is obtained via the first derivative of the function E=f(x) by means of the quantum-chemical method, with E=total energy of the precursor to the transition state and x=nuclear coordinates of the molecule in the precursor to the transition state. In step C3, the same quantum-chemical method is used as in steps B2, B3 and C2.

The further continuation of the method depends on the size of the gradient norm C3 obtained. If the gradient norm C3 $\nabla$ is $0 \leq \nabla \leq 0.03$ $E_h$ $a_0^{-1}$, step D1 of the method can be performed with the precursor to the transition state. $E_h$ here represents the Hartree energy, where 1 $E_h$=4.3597·10$^{-18}$ J, and $a_0$ represents the Bohr radius, where 1 $a_0$=5.29·10$^{-11}$ m.

If the gradient norm C3 $\nabla$ is >0.03 $E_h$ $a_0^{-1}$, steps C1 to C3 are repeated in step 4.2 until a gradient norm C3 of $0 \leq \nabla \leq 0.03$ $E_h$ $a_0^{-1}$ is obtained. The repetition of steps C1 to C3 constitutes an iterative method by which the gradient norm is to be minimized. Therefore, the starting point chosen in each case for the repetition of the method is to be a molecular geometry that already has a minimum gradient norm. In the repetition of steps C1 to C3, it is thus possible in step C1 to vary not just the optimized starting geometry but also a precursor to the transition state if the value of its gradient norm C3 is less than that of the optimized starting geometry. Preferably, the optimized starting geometry obtained in the performance of the method and precursor(s) to the transition state that are obtained and the values of the respective gradient norms C3 are stored.

If steps C1 to C3 have been performed once, it is possible to choose that molecular geometry with the lowest gradient norm from two molecular geometries to perform the repetition, namely either the optimized starting geometry or the precursor to the transition state obtained in the first run. If steps C1 to C3 have been performed once, the geometry of the precursor to the transition state is varied in step C1 when the value of its gradient norm C3 is lower than the value of the gradient norm B3 of the optimized starting geometry.

If steps C1 to C3 have already been performed, it is possible to choose that molecular geometry with the lowest gradient norm from more than two molecular geometries to perform the repetition, namely either the optimized starting geometry or the (more than one) precursor to the transition state obtained in the repetitions. If steps C1 to C3 have been performed more than once, the geometry of the optimized starting geometry or that precursor to the transition state from the preceding repetitions that has the lowest value for the gradient norm C3 or B3 compared to all the gradient norms C3 and B3 previously obtained is varied in step C1.

Preferably, in step C4.1, the gradient norm C3 is $\leq 0.02$ $E_h$ $a_0^{-1}$, more preferably C3$\leq 0.01$ $E_h$ $a_0^{-1}$, and step C4.2 is continued until a gradient norm C3$\leq 0.02$ $E_h$ $a_0^{-1}$, more preferably C3$\leq 0.01$ $E_h$ $a_0^{-1}$, is obtained.

Preferably, step C4.2 is repeated not more than 50 times, preferably not more than 40 times, more preferably not more than 30 times, even more preferably not more than 10 times, especially not more than 3 times. Preferably, in the performance of step C4.2, a different atom may be selected in the repetition of step C1 than in the preceding performance of the method.

One advantage of the method according to the invention is that, in the variation using a Monte Carlo algorithm, only the atom coordinates of the selected function space, i.e. of the subspace of the selected atoms involved in the bond dissociation or preferably synthesis reaction in question, are defined in the vector space of all atom coordinates included in the molecule, or in the molecule ensemble. This means that the Monte Carlo algorithm according to the invention operates only in this subspace since its functions are defined only therein. Thus, the subspace of the coordinates involved in the dissociation, or preferably synthesis reaction, is the function space of the Monte Carlo algorithm. The calculation of the energies and the gradient vectors (or norm thereof) depends on all the coordinates in the molecule, but the Monte Carlo algorithm according to the invention considers these only as a function of the coordinates of the subspace. In order that, in this consideration, the function value, i.e. the gradient norm to be minimized, remains clear, each consideration of the function value is preceded by relaxation of the entire molecular structure by a geometry optimization with boundary condition(s). The boundary condition(s) are the bond distances generated by the Monte Carlo algorithm.

If the gradient norm has been sufficiently minimized, the property of negative curvature in the region of the steady-state point obtained is verified by infinitesimal deflections and subsequent geometry optimization in step D. The deflection here along the bond dissociation must result in a decrease in total energy. It is a further advantage of the present invention that it is possible in this way to completely avoid the demanding calculation of the second derivatives of the energy by the nuclear coordinates.

Preferably, in step D3, the energy of the two optimized precursors (i) and (II) is expressed in the unit of the unit $E_h$ $a_0^{-1}$.

A precursor is classified as the transition state in step D4.1 when both the value of the energy of the optimized precursor (i) and the value of the energy of the optimized precursor (ii) are smaller than the value of the energy C3 or B3 of the precursor that was used in step D1. If one of the two energy values of the optimized precursor (i) or (ii) is greater, or both energy values of the optimized precursors (i) or (ii) are greater, than the energy value C3 or B3 of the precursor that was used in step D1, the method is repeated from step C. Preferably, the method from step C is repeated not more than 10 times, preferably not more than 3 times.

In steps B2, B3, C2, C3, D2 and D3, the same quantum-chemical method is used in each case. Preferably, the quantum-chemical method from steps B2, B3, C2, C3, D2 and D3 is a semiempirical method, density functional theory method or an approximation of the Schrodinger equation, especially preferably density functional theory methods, for example the TPSS density functional with a def2-SVP basis set as implemented in a standard manner in the Turbomole software package. In a preferred embodiment, the quantum-mechanical calculations are conducted with the TURBOMOLE software package. Preference is given to calculating using a computer with 16-core processors with a clock frequency of 3.20 GHz and a 25 MB cache with 128 GB of DDR4 2400 rg ECC RAM.

Preferably, the chemical reaction is a synthesis selected from the group consisting of polymer syntheses, especially polyurethane syntheses, syntheses of monomers for polymerization reactions, industrially required commodity chemicals, additives, surfactants and active pharmacological ingredients. In particular, the chemical reaction is a synthesis for commodity chemicals or reactants for chemical syntheses that are obtained with catalysts. Additives are generally understood to mean additives for plastics such as plasticizers, antioxidants, modifiers, and additives for fuels, in the synthesis of which catalysts are used in each case.

If, in the preferred embodiment of the method, at least two molecules I and II are provided, the steps mentioned under letters A, B and C of the method may preferably be repeated, wherein, in each repetition by comparison with preceding performances of the method, molecule I is varied or a different molecule is provided as molecule I, and molecule II is not varied, nor is any other molecule provided as molecule II, and the additional step D0 is conducted:

D0 comparing the gradient norm C3 obtained in the repetitions for the various precursors to the transition state and selecting the precursor to the transition state having the lowest gradient norm C3 and performing step D1 and/or D2 with the selected precursor to the transition state.

In this above-described preferred embodiment of the method, the gradient norm C3 is first calculated for different combinations of molecules and the results are stored. Then, in a preferred step D0, the values obtained for the gradient norm C3 may be compared and the combination of molecules with the lowest gradient norm C3 may be selected. This preferred embodiment of the method thus enables direct comparison of different combinations of molecules.

The invention further provides a system for data processing, comprising means of executing a method according to the invention.

The invention further provides a computer program and a computer-readable storage medium comprising commands that, on execution of the program by a computer, cause it to perform the following steps of a method:

A Generating a Starting Geometry
  A1 providing the three-dimensional representation of at least one molecule at ground state energy,
  A2 selecting at least one bond of the at least one molecule and selecting a length of the bond, where the selected length does not correspond to the length of the bond at ground state energy of the molecule, such that a starting geometry for the chemical reaction is obtained,
  A3 representing the starting geometry in three dimensions in Cartesian and/or internal coordinates, B Ascertaining an Optimized Starting Geometry
  B1 defining a function space encompassing the at least one bond from step A2 and the atoms joined by this bond,
  B2 optimizing the geometry of the function space selected in step B1 by means of a quantum-chemical method and with the boundary condition that the length of the at least one bond selected in step A2 is kept constant, such that an optimized starting geometry is obtained,
  B3 ascertaining the gradient norm B3 for the optimized starting geometry, where the gradient norm is obtained via the first derivative of a function $E=f(x)$ of the quantum-chemical method and, with $E$=total energy of the optimized starting geometry and $x$=nuclear coordinates of the molecule in the optimized starting geometry,
  B4.1 when the gradient norm B3 $\nabla$ is $0 \leq \nabla \leq 0.03$ $E_h$ $a_0^{-1}$, classifying the optimized starting geometry as a precursor to the transition state of the chemical reaction and continuing the method with step D1, or
  B4.2 when the gradient norm B3 $\nabla$ is $>0.03$ $E_h$ $a_0^{-1}$, ascertaining the precursor to the transition state of the chemical reaction proceeding from the optimized starting geometry by a method comprising the following steps:

C Ascertaining the Precursor to the Transition State of the Chemical Reaction
  C1 varying the optimized starting geometry using a Monte Carlo algorithm, wherein
    C1.1 at least one atom from the function space selected in step B1 is selected at random,
    C1.2 a vector for a deflection of the atom chosen in step C1 is selected at random, weighting the randomly chosen magnitude of the vector by the gradient norm B3,
    C1.3 the atom selected in step C1.1 is deflected from the position of the atom in the optimized starting geometry using the vector from step C1.2, so as to obtain a precursor to a transition state of the chemical reaction,
  C2 optimizing the geometry of the precursor to the transition state by means of the quantum-chemical method and with the boundary condition that the at least one bond from step A2 has the length that was ascertained in step C3,
  C3 ascertaining the gradient norm C3 for the precursor to the transition state from step C2, where the gradient norm is obtained via the first derivative of the function $E=f(x)$ of the quantum-chemical method and, with $E$=total energy of the precursor to the transition state and $x$=nuclear coordinates of the molecule in the precursor to the transition state,
  C4.1 when the gradient norm C3 $\nabla$ is $0 \leq \nabla \leq 0.03$ $E_h$ $a_0^{-1}$, continuing the method with step D1, or
  C4.2 when the gradient norm C3 $\nabla > 0.03$ $E_h$ $a_0^{-1}$ $E_h$ $a_0^{-1}$, repeating steps C1 to C3 until a gradient norm C3 $\nabla$ of $0 \leq \nabla \leq 0.03$ $E_h$ $a_0^{-1}$ is obtained, wherein
    (a) if steps C1 to C3 have been performed once, the geometry of the precursor to the transition state is varied in step C1 when the value of its gradient norm C3 is lower than the value of the gradient norm B3 of the optimized starting geometry, or
    (b) if steps C1 to C3 have been performed more than once, the geometry of the optimized starting geometry or that precursor to the transition state from the preceding repetitions that has the lowest value for the gradient norm C3 or B3 compared to all the gradient norms C3 and B3 previously obtained is varied in step C1, D Ascertaining the Transition State
  D1 varying the precursor from step C4.1 or the precursor from step B4.1 by performing the following steps for one atom within the function space defined in B1:
    D1.1 selecting an atom from the function space selected in step B1,
    D1.2 selecting a vector for a deflection of the atom chosen in step D1.1,
    D1.3 deflecting the atom selected in step D1.1 using the vector from step D1.2 from its position in the precursor, wherein the position is deflected once by the positive value of the magnitude of the vector and once by the negative value of the magnitude of the vector, such that two deflected precursors are obtained when steps D1.1 to D1.3 are conducted,
  D2 optimizing the geometry of the two deflected precursors from step D1 by means of the quantum-chemical method under the constraint that the bond distances obtained in D1 are kept constant, such that two optimized precursors (i) and (ii) are obtained,
  D3 calculating the energy of the two optimized precursors (i) and (ii) from step D2 by means of the quantum-chemical method,
  D4 comparing the energy values of the two optimized precursors with the energy value C3 or B3 of the precursor that was used in step D1,
  D4.1. if the energy value of the optimized precursor (i) and the energy value of the optimized precursor (ii) are each smaller than the energy value C3 or B3 of the precursor that was used in step D1, classifying the precursor that was used in step D1 as the transition state,
  D4.2. if the energy value of the optimized precursor (i) or the energy value of the optimized precursor (ii) is not smaller than the energy value C3 or B3 of the precursor that was used in step D1, repeating the method from step C1.

Preferably, the computer program and/or the computer-readable storage medium comprises commands that, on execution of the program by a computer, cause it to perform steps B to D of the method.

The invention is further directed to the use of the computer program according to the invention or of the computer-readable storage medium according to the invention for assessing transition states of a chemical reaction, especially a polymer synthesis.

The invention especially relates to the following embodiments:

In a first embodiment, the invention relates to a computer-implemented method of calculating transition states of a chemical reaction, comprising the steps of:

A Generating a Starting Geometry
- A1 providing the three-dimensional representation of at least one molecule at ground state energy,
- A2 selecting at least one bond of the at least one molecule and selecting a length of the bond, where the selected length does not correspond to the length of the bond at ground state energy of the molecule, such that a starting geometry for the chemical reaction is obtained,
- A3 representing the starting geometry in three dimensions in Cartesian and/or internal coordinates, B Ascertaining an Optimized Starting Geometry
- B1 defining a function space encompassing the at least one bond from step A2 and the atoms joined by this bond,
- B2 optimizing the geometry of the function space selected in step B1 by means of a quantum-chemical method and with the boundary condition that the length of the at least one bond selected in step A2 is kept constant, such that an optimized starting geometry is obtained,
- B3 ascertaining the gradient norm B3 for the optimized starting geometry, where the gradient norm is obtained via the first derivative of a function $E=f(x)$ of the quantum-chemical method and, with E=total energy of the optimized starting geometry and x=nuclear coordinates of the molecule in the optimized starting geometry,
- B4.1 when the gradient norm B3 $\nabla$ is $0 \leq \nabla \leq 0.03$ $E_h$ $a_0^{-1}$, classifying the optimized starting geometry as a precursor to the transition state of the chemical reaction and continuing the method with step D1, or
- B4.2 when the gradient norm B3 $\nabla$ is $>0.03$ $E_h$ $a_0^{-1}$, ascertaining the precursor to the transition state of the chemical reaction proceeding from the optimized starting geometry by a method comprising the following steps:

C Ascertaining the Precursor to the Transition State of the Chemical Reaction
- C1 varying the optimized starting geometry using a Monte Carlo algorithm, wherein
- C1.1 at least one atom from the function space selected in step B1 is selected at random,
- C1.2 a vector for a deflection of the atom chosen in step C1 is selected at random, weighting the randomly chosen magnitude of the vector by the gradient norm B3,
- C1.3 the atom selected in step C1.1 is deflected from the position of the atom in the optimized starting geometry using the vector from step C1.2, so as to obtain a precursor to a transition state of the chemical reaction,
- C2 optimizing the geometry of the precursor to the transition state by means of the quantum-chemical method and with the boundary condition that the at least one bond from step A2 has the length that was ascertained in step C3,
- C3 ascertaining the gradient norm C3 for the precursor to the transition state from step C2, where the gradient norm is obtained via the first derivative of the function $E=f(x)$ of the quantum-chemical method and, with E=total energy of the precursor to the transition state and x=nuclear coordinates of the molecule in the precursor to the transition state, C4.1 when the gradient norm C3 $\nabla$ is $0 \leq \nabla \leq 0.03$ $E_h$ $a_0^{-1}$, continuing the method with step D1, or C4.2 when the gradient norm C3$\nabla$>0.03 $E_h$ $a_0^{-1}$ $E_h$ $a_0^{-1}$, repeating steps C1 to C3 until a gradient norm C3 $\nabla$ of $0 \leq \nabla \leq 0.03$ $E_h$ $a_0^{-1}$ is obtained, wherein
  - (a) if steps C1 to C3 have been performed once, the geometry of the precursor to the transition state is varied in step C1 when the value of its gradient norm C3 is lower than the value of the gradient norm B3 of the optimized starting geometry, or
  - (b) if steps C1 to C3 have been performed more than once, the geometry of the optimized starting geometry or that precursor to the transition state from the preceding repetitions that has the lowest value for the gradient norm C3 or B3 compared to all the gradient norms C3 and B3 previously obtained is varied in step C1, D Ascertaining the Transition State
- D1 varying the precursor from step C4.1 or the precursor from step B4.1 by performing the following steps for one atom within the function space defined in B1:
- D1.1 selecting an atom from the function space selected in step B1,
- D1.2 selecting a vector for a deflection of the atom chosen in step D1.1,
- D1.3 deflecting the atom selected in step D1.1 using the vector from step D1.2 from its position in the precursor, wherein the position is deflected once by the positive value of the magnitude of the vector and once by the negative value of the magnitude of the vector, such that two deflected precursors are obtained when steps D1.1 to D1.3 are conducted,
- D2 optimizing the geometry of the two deflected precursors from step D1 by means of the quantum-chemical method under the constraint that the bond distances obtained in D1 are kept constant, such that two optimized precursors (i) and (ii) are obtained,
- D3 calculating the energy of the two optimized precursors (i) and (ii) from step D2 by means of the quantum-chemical method,
- D4 comparing the energy values of the two optimized precursors with the energy value C3 or
- B3 of the precursor that was used in step D1,
- D4.1. if the energy value of the optimized precursor (i) and the energy value of the optimized precursor (ii) are each smaller than the energy value C3 or B3 of the precursor that was used in step D1, classifying the precursor that was used in step D1 as the transition state,
- D4.2. if the energy value of the optimized precursor (i) or the energy value of the optimized precursor (ii) is not smaller than the energy value C3 or B3 of the precursor that was used in step D1, repeating the method from step C1.

In a second embodiment, the invention relates to a method according to Embodiment 1, characterized in that the at least one molecule from step A1 has a size of more than 100 atoms and/or in that the length of the bond selected in step A2 is not more than 230 pm.

In a third embodiment, the invention relates to a method according to either of Embodiments 1 and 2, characterized in that step C1.2 comprises the further following steps:
C1.2a determining a further atom from the function space selected in step B1 which does not correspond to the atom selected in step C1.1,
C1.2b selecting the direction of the vector, where the position of the atom selected in step C1.2.a determines the direction of the vector,
C1.2.c randomly selecting the length of the vector, where the value of the length of the vector may assume positive or negative values.

In a fourth embodiment, the invention relates to a method according to any of the preceding embodiments, characterized in that the weighting of the randomly selected magnitude of the vector in step C1.2 is effected by multiplying the numerical value of the randomly selected magnitude of the vector by the numerical value of the gradient norm B3.

In a fifth embodiment, the invention relates to a method according to any of the preceding embodiments, characterized in that, in step C4.1, the gradient norm C3 is $\leq 0.02$ $E_h$ $a_0^{-1}$, preferably $\leq 0.01$ $E_h$ $a_0^{-1}$, and step C4.2 is continued until a gradient norm C3$\leq 0.02$ $E_h$ $a_0^{-1}$, preferably $\leq 0.01$ $E_h$ $a_0^{-1}$, is obtained.

In a sixth embodiment, the invention relates to a method according to any of the preceding embodiments, characterized in that step C4.2 is repeated not more than 50 times, preferably not more than 30 times, especially not more than 3 times.

In a seventh embodiment, the invention relates to a method according to any of the preceding embodiments, characterized in that, in the performance of step C4.2, a different atom may be selected in the repetition of step C1 than in the preceding performance of the method.

In an eighth embodiment, the invention relates to a method according to any of the preceding embodiments, characterized in that the quantum-chemical method from steps B2, B3, C2, C3, D2 and D3 is a semiempirical method, density functional theory method or an approximation of the Schrödinger equation, the quantum-chemical method from steps B2, B3, C2, C3, D2 and D3 especially being a density functional theory method.

In a ninth embodiment, the invention relates to a method according to any of the preceding embodiments, characterized in that the chemical reaction is a synthesis selected from the group consisting of polymer syntheses, especially polyurethane syntheses, syntheses of monomers for polymerization reactions, industrially required commodity chemicals, platform chemicals, additives, surfactants and active pharmacological ingredients.

In a tenth embodiment, the invention relates to a method according to any of the preceding embodiments, characterized in that, in step A1, at least two molecules I and II are provided and, in step A2, alternatively or additionally to the at least one bond, at least one distance between at least one atom from molecule I and at least one atom from molecule II and the length of the at least one distance are also selected, where the length of the distance is especially not more than 230 pm.

In an eleventh embodiment, the invention relates to a method according to Embodiment 10, characterized in that the steps mentioned under letters A, B and C of the method are repeated, wherein, in each repetition by comparison with preceding performances of the method, molecule I is varied or a different molecule is provided as molecule I, and molecule II is not varied, nor is any other molecule provided as molecule II, and comprising the additional step of:
D0 comparing the gradient norm C3 obtained in the repetitions for the various precursors to the transition state and selecting the precursor to the transition state having the lowest gradient norm C3 and performing step D1 and/or D2 with the selected precursor to the transition state.

In a twelfth embodiment, the invention relates to a method according to either of Embodiments 10 and 11, characterized in that molecule I is a catalyst for the chemical reaction, especially for a polymer synthesis, and molecule II is a reactant in the chemical reaction.

In a thirteenth embodiment, the invention relates to a method according to any of Embodiments 10 to 13, characterized in that molecule I has a size of 2 to 1000 atoms and molecule II has a size of 2 to 1000 atoms, and the sum total of the atoms from molecule I and from molecule II should preferably be more than 100 atoms.

In a fourteenth embodiment, the invention relates to system for data processing, comprising means of executing a method comprising the steps of:
A Generating a Starting Geometry
  A1 providing the three-dimensional representation of at least one molecule at ground state energy,
  A2 selecting at least one bond of the at least one molecule and selecting a length of the bond, where the selected length does not correspond to the length of the bond at ground state energy of the molecule, such that a starting geometry for the chemical reaction is obtained,
  A3 representing the starting geometry in three dimensions in Cartesian and/or internal coordinates,
B Ascertaining an Optimized Starting Geometry
  B1 defining a function space encompassing the at least one bond from step A2 and the atoms joined by this bond,
  B2 optimizing the geometry of the function space selected in step B1 by means of a quantum-chemical method and with the boundary condition that the length of the at least one bond selected in step A2 is kept constant, such that an optimized starting geometry is obtained,
  B3 ascertaining the gradient norm B3 for the optimized starting geometry, where the gradient norm is obtained via the first derivative of a function E=f(x) of the quantum-chemical method and, with E=total energy of the optimized starting geometry and x=nuclear coordinates of the molecule in the optimized starting geometry,
  B4.1 when the gradient norm B3 $\nabla$ is $0 \leq \nabla \leq 0.03$ $E_h$ $a_0^{-1}$, classifying the optimized starting geometry as a precursor to the transition state of the chemical reaction and continuing the method with step D1, or
  B4.2 when the gradient norm B3 $\nabla$ is $>0.03$ $E_h$ $a_0^{-1}$, ascertaining the precursor to the transition state of the chemical reaction proceeding from the optimized starting geometry by a method comprising the following steps:
C Ascertaining the Precursor to the Transition State of the Chemical Reaction
  C1 varying the optimized starting geometry using a Monte Carlo algorithm, wherein
  C1.1 at least one atom from the function space selected in step B1 is selected at random, C1.2 a vector for a deflection of the atom chosen in step C1 is selected at random, weighting the randomly chosen magnitude of the vector by the gradient norm B3, C1.3 the atom selected in step C1.1 is deflected from the position of the atom in the optimized starting geometry using the vector from step C1.2, so as to obtain a precursor to a transition state of the chemical reaction, C2 optimizing the geometry of the precursor to the transition state by means of the quantum-chemical method and with the boundary condition that the at least one bond from step A2 has the length that was ascertained in step C3, C3 ascertaining the gradient norm C3 for the precursor to the transition state from step C2, where the gradient norm is obtained via the first derivative of the function E=f(x) of the quantum-chemical method and, with E=total energy of the precursor to the transition state and x=nuclear coordinates of the molecule in the precursor to the transition state, C4.1 when the gradient norm C3 $\nabla$ is $0 \leq \nabla \leq 0.03$ $E_h$ $a_0^{-1}$, continuing the method with step D1, or C4.2 when the gradient norm C3$\nabla$>0.03 $E_h$ $a_0^{-1}$ $E_h$ $a_0^{-1}$, repeating steps C1 to C3 until a gradient norm C3 V of $0 \leq \nabla \leq 0.03$ $E_h$ $a_0^{-1}$ is obtained, wherein
  (a) if steps C1 to C3 have been performed once, the geometry of the precursor to the transition state is varied in step C1 when the value of its gradient norm C3 is lower than the value of the gradient norm B3 of the optimized starting geometry, or
  (b) if steps C1 to C3 have been performed more than once, the geometry of the optimized starting geometry or that precursor to the transition state from the preceding repetitions that has the lowest value for the gradient norm C3 or B3 compared to all the gradient norms C3 and B3 previously obtained is varied in step C1, D Ascertaining the Transition State
  D1 varying the precursor from step C4.1 or the precursor from step B4.1 by performing the following steps for one atom within the function space defined in B1:
  D1.1 selecting an atom from the function space selected in step B1,
  D1.2 selecting a vector for a deflection of the atom chosen in step D1.1,
  D1.3 deflecting the atom selected in step D1.1 using the vector from step D1.2 from its position in the precursor, wherein the position is deflected once by the positive value of the magnitude of the vector and once by the negative value of the magnitude of the vector, such that two deflected precursors are obtained when steps D1.1 to D1.3 are conducted,
  D2 optimizing the geometry of the two deflected precursors from step D1 by means of the quantum-chemical method under the constraint that the bond distances obtained in D1 are kept constant, such that two optimized precursors (i) and (ii) are obtained,
  D3 calculating the energy of the two optimized precursors (i) and (ii) from step D2 by means of the quantum-chemical method,
  D4 comparing the energy values of the two optimized precursors with the energy value C3 or B3 of the precursor that was used in step D1,
  D4.1. if the energy value of the optimized precursor (i) and the energy value of the optimized precursor (ii) are each smaller than the energy value C3 or B3 of the precursor that was used in step D1, classifying the precursor that was used in step D1 as the transition state,
  D4.2. if the energy value of the optimized precursor (i) or the energy value of the optimized precursor (ii) is not smaller than the energy value C3 or B3 of the precursor that was used in step D1, repeating the method from step C1.

In a fifteenth embodiment, the invention relates to a computer program comprising commands that, on execution of the program by a computer, cause it to perform the following steps of a method:

A Generating a Starting Geometry
  A1 providing the three-dimensional representation of at least one molecule at ground state energy,
  A2 selecting at least one bond of the at least one molecule and selecting a length of the bond, where the selected length does not correspond to the length of the bond at ground state energy of the molecule, such that a starting geometry for the chemical reaction is obtained,
  A3 representing the starting geometry in three dimensions in Cartesian and/or internal coordinates, B Ascertaining an Optimized Starting Geometry
  B1 defining a function space encompassing the at least one bond from step A2 and the atoms joined by this bond,
  B2 optimizing the geometry of the function space selected in step B1 by means of a quantum-chemical method and with the boundary condition that the length of the at least one bond selected in step A2 is kept constant, such that an optimized starting geometry is obtained,
  B3 ascertaining the gradient norm B3 for the optimized starting geometry, where the gradient norm is obtained via the first derivative of a function E=f(x) of the quantum-chemical method and, with E=total energy of the optimized starting geometry and x=nuclear coordinates of the molecule in the optimized starting geometry,
  B4.1 when the gradient norm B3 $\nabla$ is $0 \leq \nabla \leq 0.03$ $E_h$ $a_0^{-1}$, classifying the optimized starting geometry as a precursor to the transition state of the chemical reaction and continuing the method with step D1, or
  B4.2 when the gradient norm B3 $\nabla$ is >0.03 $E_h$ $a_0^{-1}$, ascertaining the precursor to the transition state of the chemical reaction proceeding from the optimized starting geometry by a method comprising the following steps:

C Ascertaining the Precursor to the Transition State of the Chemical Reaction
  C1 varying the optimized starting geometry using a Monte Carlo algorithm, wherein
  C1.1 at least one atom from the function space selected in step B1 is selected at random,
  C1.2 a vector for a deflection of the atom chosen in step C1 is selected at random, weighting the randomly chosen magnitude of the vector by the gradient norm B3,
  C1.3 the atom selected in step C1.1 is deflected from the position of the atom in the optimized starting geometry using the vector from step C1.2, so as to obtain a precursor to a transition state of the chemical reaction,
  C2 optimizing the geometry of the precursor to the transition state by means of the quantum-chemical method and with the boundary condition that the at least one bond from step A2 has the length that was ascertained in step C3, C3 ascertaining the gradient norm C3 for the precursor to the transition state from step C2, where the gradient norm is obtained via the first derivative of the function E=f(x) of the quantum-chemical method and, with E=total energy of the precursor to the transition state and x=nuclear coordinates of the molecule in the precursor to the transition state, C4.1 when the gradient norm C3 $\nabla$ is $0 \leq \nabla \leq 0.03$ $E_h$ $a_0^{-1}$, continuing the method with step D1, or C4.2 when the gradient norm C3$\nabla$>0.03 $E_h$ $a_0^{-1}$ $E_h$ $a_0^{-1}$, repeating steps C1 to C3 until a gradient norm C3 $\nabla$ of $0 \leq \nabla \leq 0.03$ $E_h$ $a_0^{-1}$ is obtained, wherein (a) if steps C1 to C3 have been performed once, the geometry of the precursor to the transition state is varied in step C1 when the value of its gradient norm C3 is lower than the value of the gradient norm B3 of the optimized starting geometry, or (b) if steps C1 to C3 have been performed more than once, the geometry of the optimized starting geometry or that precursor to the transition state from the preceding repetitions that has the lowest value for the gradient norm C3 or B3 compared to all the gradient norms C3 and B3 previously obtained is varied in step C1, D Ascertaining the Transition State D1 varying the precursor from step C4.1 or the precursor from step B4.1 by performing the following steps for one atom within the function space defined in B1:

D1.1 selecting an atom from the function space selected in step B1,

D1.2 selecting a vector for a deflection of the atom chosen in step D1.1,

D1.3 deflecting the atom selected in step D1.1 using the vector from step D1.2 from its position in the precursor, wherein the position is deflected once by the positive value of the magnitude of the vector and once by the negative value of the magnitude of the vector, such that two deflected precursors are obtained when steps D1.1 to D1.3 are conducted, D2 optimizing the geometry of the two deflected precursors from step D1 by means of the quantum-chemical method under the constraint that the bond distances obtained in D1 are kept constant, such that two optimized precursors (i) and (ii) are obtained, D3 calculating the energy of the two optimized precursors (i) and (ii) from step D2 by means of the quantum-chemical method, D4 comparing the energy values of the two optimized precursors with the energy value C3 or B3 of the precursor that was used in step D1, D4.1. if the energy value of the optimized precursor (i) and the energy value of the optimized precursor (ii) are each smaller than the energy value C3 or B3 of the precursor that was used in step D1, classifying the precursor that was used in step D1 as the transition state, D4.2. if the energy value of the optimized precursor (i) or the energy value of the optimized precursor (ii) is not smaller than the energy value C3 or B3 of the precursor that was used in step D1, repeating the method from step C1.

In a sixteenth embodiment, the invention relates to a computer-readable storage medium comprising commands that, on execution by a computer, cause it to perform the following steps of a method:

A Generating a Starting Geometry

A1 providing the three-dimensional representation of at least one molecule at ground state energy, A2 selecting at least one bond of the at least one molecule and selecting a length of the bond, where the selected length does not correspond to the length of the bond at ground state energy of the molecule, such that a starting geometry for the chemical reaction is obtained, A3 representing the starting geometry in three dimensions in Cartesian and/or internal coordinates, B Ascertaining an Optimized Starting Geometry B1 defining a function space encompassing the at least one bond from step A2 and the atoms joined by this bond, B2 optimizing the geometry of the function space selected in step B1 by means of a quantum-chemical method and with the boundary condition that the length of the at least one bond selected in step A2 is kept constant, such that an optimized starting geometry is obtained, B3 ascertaining the gradient norm B3 for the optimized starting geometry, where the gradient norm is obtained via the first derivative of a function E=f(x) of the quantum-chemical method and, with E=total energy of the optimized starting geometry and x=nuclear coordinates of the molecule in the optimized starting geometry, B4.1 when the gradient norm B3 $\nabla$ is $0 \leq \nabla \leq 0.03$ $E_h$ $a_0^{-1}$, classifying the optimized starting geometry as a precursor to the transition state of the chemical reaction and continuing the method with step D1, or B4.2 when the gradient norm B3 $\nabla$ is >0.03 $E_h$ $a_0^{-1}$, ascertaining the precursor to the transition state of the chemical reaction proceeding from the optimized starting geometry by a method comprising the following steps:

C Ascertaining the Precursor to the Transition State of the Chemical Reaction

C1 varying the optimized starting geometry using a Monte Carlo algorithm, wherein C1.1 at least one atom from the function space selected in step B1 is selected at random, C1.2 a vector for a deflection of the atom chosen in step C1 is selected at random, weighting the randomly chosen magnitude of the vector by the gradient norm B3, C1.3 the atom selected in step C1.1 is deflected from the position of the atom in the optimized starting geometry using the vector from step C1.2, so as to obtain a precursor to a transition state of the chemical reaction, C2 optimizing the geometry of the precursor to the transition state by means of the quantum-chemical method and with the boundary condition that the at least one bond from step A2 has the length that was ascertained in step C3, C3 ascertaining the gradient norm C3 for the precursor to the transition state from step C2, where the gradient norm is obtained via the first derivative of the function E=f(x) of the quantum-chemical method and, with E=total energy of the precursor to the transition state and x=nuclear coordinates of the molecule in the precursor to the transition state, C4.1 when the gradient norm C3 $\nabla$ is $0 \leq \nabla \leq 0.03$ $E_h$ $a_0^{-1}$, continuing the method with step D1, or C4.2 when the gradient norm C3$\nabla$>0.03 $E_h$ $a_0^{-1}$ $E_h$ $a_0^{-1}$, repeating steps C1 to C3 until a gradient norm C3 $\nabla$ of $0 \leq \nabla \leq 0.03$ $E_h$ $a_0^{-1}$ is obtained, wherein (a) if steps C1 to C3 have been performed once, the geometry of the precursor to the transition state is varied in step C1 when the value of its gradient norm C3 is lower than the value of the gradient norm B3 of the optimized starting geometry, or (b) if steps C1 to C3 have been performed more than once, the geometry of the optimized starting geometry or that precursor to the transition state from the preceding repetitions that has the lowest value for the gradient norm C3 or B3 compared to all the gradient norms C3 and B3 previously obtained is varied in step C1, D Ascertaining the Transition State D1 varying the precursor from step C4.1 or the precursor from step B4.1 by performing the following steps for one atom within the function space defined in B1:

D1.1 selecting an atom from the function space selected in step B1,

D1.2 selecting a vector for a deflection of the atom chosen in step D1.1,

D1.3 deflecting the atom selected in step D1.1 using the vector from step D1.2 from its position in the precursor, wherein the position is deflected once by the positive value of the magnitude of the vector and once by the negative value of the magnitude of the vector, such that two deflected precursors are obtained when steps D1.1 to D1.3 are conducted, D2 optimizing the geometry of the two deflected precursors from step D1 by means of the quantum-chemical method under the constraint that the bond distances obtained in D1 are kept constant, such that two optimized precursors (i) and (ii) are obtained, D3 calculating the energy of the two optimized precursors (i) and (ii) from step D2 by means of the quantum-chemical method, D4 comparing the energy values of the two optimized precursors with the energy value C3 or B3 of the precursor that was used in step D1, D4.1. if the energy value of the optimized precursor (i) and the energy value of the optimized precursor (ii) are each smaller than the energy value C3 or B3 of the precursor that was used in step D1, classifying the precursor that was used in step D1 as the transition state, D4.2. if the energy value of the optimized precursor (i) or the energy value of the optimized precursor (ii) is not smaller than the energy value C3 or B3 of the precursor that was used in step D1, repeating the method from step C1.

In a seventeenth embodiment, the invention relates to the use of a computer program according to Embodiment 15 or of a computer-readable storage medium according to Embodiment 16 for evaluating transition states of a chemical reaction, especially a polymer synthesis.

In an eighteenth embodiment, the invention relates to methods according to any of the first to thirteenth embodiments, characterized in that information as to the transition state ascertained in step D.1 and/or the equilibrium state ascertained in step D.2 is communicated to a user.

In a nineteenth embodiment, the invention relates to methods according to any of the first to thirteenth embodiments, characterized in that information as to the transition state ascertained in step D.1 and/or the equilibrium state ascertained in step D.2 is received by a user.

In a twentieth embodiment, the invention relates to methods according to any of the ninth to thirteenth embodiments, characterized in that the molecule I is synthesized after step D.1 and/or after step D.2.

In a twenty-first embodiment, the invention relates to methods according to any of the ninth to thirteenth embodiments, characterized in that after step D.1 and/or after step D.2 by a chemical reaction with molecule I as catalyst is performed.

In a twenty-second embodiment, the invention relates to methods according to any of the ninth to thirteenth or twenty-first embodiments, characterized in that after step D.1 and/or after step D.2 by a chemical reaction with molecule II as co-reactant is performed.

The invention is to be illustrated by the examples that follow, but without being limited thereto.

The activity of various catalysts for the reaction of a prepolymer having terminal isocyanate groups with water was examined. For this purpose, first of all, with the aid of the method according to the invention, the activation energies for reaction with the respective catalyst were calculated. The values calculated were then compared with the results of laboratory experiments for the reactions calculated beforehand. The yardstick used for the activity of the catalysts tested in the laboratory experiments was the reaction temperature above which the catalysts showed activity. Whether the catalysts showed activity was determined in the laboratory experiment by the release of gases and the foaming of the reaction mixture.

The Laboratory Experiments were Performed as Follows:

Synthesis of an HDI Prepolymer with Terminal Isocyanate Groups

Since commercial prepolymers contain residues of catalysts that could distort the experimental result, a prepolymer was synthesized for the performance of the experiments. For this purpose, under an argon countercurrent, 20.00 g (48.193 mmol; 1.0 equivalent) of a polypropylene glycol (PET1004) having an average molecular weight of 415 g/mol was initially charged, and 16.212 g of hexamethylene diisocyanate (2.0 equivalents) was added. The mixture was heated to 80° C. while stirring over a period of 3 h. After cooling to room temperature and storage of the product at room temperature for one week, a transparent viscous substance was obtained. The number-average molecular weight of the HDI prepolymer was ascertained with the aid of gel permeation chromatography. The sample was analysed in THF with polystyrene as standard on a GPC column of the PSS SDV 5 μm linear S THF type. This ascertained a molecular mass of Mn=789.7.

(The theoretical molecular masses are 751.4 g/mol in the case of extension of the polypropylene glycol used with HDI twice, and 583.2 g/mol in the case of a single extension of the polypropylene glycol used with HDI).

Test Reactions

The following catalysts were used for each of the reactions of the HDI prepolymer with water:

DBN: 1,5-diazabicyclo [4,3,0]non-5-ene;

NEt$_3$: triethylamine;

DMA: dimethylaniline

A test tube with a magnetic stirrer was charged with 1.0 equivalent of HDI prepolymer and 2.0 equivalents of water. The contents of the test tube were mixed thoroughly and 0.1 equivalent of the respective catalyst was added while stirring. The temperature of the mixture was increased gradually with the aid of an oil bath with a thermostat until distinct evolution of gas was observable.

TABLE 1

Molar masses and molar amounts of the substances used

| Component | M [g/mol] | n [mol] | m [mg] | Eq | d [g/ml] | V [ml] |
|---|---|---|---|---|---|---|
| HDI prepolymer | 751.4[1] | 5.857 | 4401 | 1.0 | — | — |
| $H_2O$ | 18.015 | 11.720 | 211 | 2.0 | 1.00 | 0.21 |
| DBN | 124.18 | 0.586 | 73 | 0.1 | 1.01 | 0.07 |
| $NEt_3$ | 101.19 | 0.586 | 59 | 0.1 | 0.73 | 0.08 |
| DMA | 121.18 | 0.586 | 71 | 0.1 | 0.96 | 0.07 |

[1]Theoretical molecular weight for a prepolymer formed from two equivalents of HDI and one equivalent of the polypropylene glycol used.

Performance of the Quantum-Mechanical Calculations

The quantum-mechanical calculations were conducted with the Turbomole software package. The density functional theory method used was the TPSS density functional with a def2-SVP basis set, as implemented as standard in the Turbomole software package. For this purpose, the computer used was an Intel Xeon E5-2667v4 with 16-core processors with a clock frequency of 3.20 GHz and a 25 MB cache with 128 GB of DDR4 2400 rg ECC RAM. The calculations were executed on two processors in each case, with provision of a storage volume of 8000 MB.

For every reaction studied, a starting geometry was chosen as a starting point for the ascertaining of a transition state. The time taken for the calculation of the respective activation energies was up to 36 hours.

For simulation of the activation energies, the reaction of a prepolymer containing two terminal, HDI-based isocyanate groups and a syntactic polypropylene glycol having seven repeat units based on propylene oxide, consist of 121 atoms in total, one molecule of water and the respective catalyst was considered (between 144 and 146 atoms in total). For generation of the starting geometries of the working examples in Table 3, in the example of DBN, in method step A1, one molecule of the prepolymer, one molecule of the DBN catalyst and one molecule of water were drawn with a suitable program for visualization of three-dimensional molecular structures. The position of the carbon atom of the isocyanate group in question, in method step A2, was placed at a distance of 175.5 pm from the oxygen atom of the water molecule in question, and one of the hydrogen atoms in the water molecule was placed at a distance of 117.4 pm from the oxygen of the water molecule. The molecular geometry thus generated, in method step A3, was stored in a representation of Cartesian coordinates, and the atoms involved in this arrangement of bond distances was used to define the function space in method step B1.

The method according to the invention was able to give the activation energies shown in Table 2.

With the aid of the pseudo-Newton-Raphson-based method known in the art for optimization of transition states, it was not possible under the same conditions, i.e. with the same starting geometries for the transition state, to obtain a transition state and hence an activation energy in any of the cases described.

TABLE 2

Collation of experimental and calculated activation energies

| Catalyst | Activation energy calculated [kcal/mol] | Temperature at which activation of the catalyst was observed in the laboratory experiment [0° C.] | Gradient norm of the optimized starting geometry [$E_h \, a_0^{-1}$] | Gradient norm of the transition state [$E_h \, a_0^{-1}$] |
|---|---|---|---|---|
| DBN | 13.2 | 23 | 0.024810 | 0.009638 |
| $NEt_3$ | 16.8 | 40 | 0.019049 | 0.006762 |
| DMA | 20.4 | 110-174[1] | 0.029652 | 0.008176 |

[1]very indistinct temperature point. Reaction barely discernible.

The data from Table 2 show that, with the aid of the method according to the invention, it is possible to calculate the molecular geometry of a transition state of a chemical reaction with very little user effort and sufficient precision that it is possible to reach a correct conclusion as to the kinetics of the chemical reaction using the activation energy calculated.

The number-average molecular weight of the HDI prepolymer that was used in the laboratory experiments is within the same range as the theoretical calculated mass of a polypropylene glycol that has been extended with HDI twice. The laboratory experiments are thus similar to the reaction conditions that were employed for calculation of the activation energy for the simulation of the reaction and give a realistic reflection of the simulation.

The activation energy for DBN calculated on the basis of the method according to the invention was somewhat lower than for $NEt_3$ and much lower than that for DMA. The conclusion can be drawn from the results calculated that DBN as catalyst in the reaction of the HDI prepolymer with water enables a transition state having lower energy than in the case of use of $NEt_3$ or DMA as catalyst. Consequently, in the performance of the reaction with DBN as catalyst, it was necessary to supply less energy (proceeding from room temperature), if any, for the reaction to proceed and products to be obtained.

These conclusions from the calculated activation energies are reflected in the results of the laboratory experiments. While the reaction of the HDI prepolymer with water and DBN as catalyst proceeded even at 23° C., it was necessary to heat the reaction mixture to 40° C. in the case of use of $NEt_3$ as catalyst. It was already possible to draw the conclusion from the activation energies calculated that a higher activation energy would be required for the performance of the reaction with $NEt_3$.

The same applies to the use of DMA as catalyst. The activation energy calculated was distinctly higher here than in the case of $NEt_3$ as catalyst. This result was able to be verified by the laboratory experiments. In the case of use of $NEt_3$ as catalyst, it was possible to see a reaction, and only a weak one, only at a temperature of more than 100° C.

The invention claimed is:

1. A method for performing a catalyzed chemical reaction, said method comprising:
    selecting a catalyst and/or a co-reactant for said chemical reaction, and
    performing said chemical reaction,
    wherein the catalyst and/or the co-reactant in said chemical reaction is selected based on calculating one or more transition states of said chemical reaction, and
    wherein calculating said one or more transition states of said chemical reaction comprises:

A Generating a starting geometry by
A1 providing a three-dimensional representation of at least one molecule at ground state energy,
A2 selecting at least one bond of the at least one molecule and selecting a length of the bond, where the selected length does not correspond to the length of the bond at ground state energy of the molecule, such that a starting geometry for the chemical reaction is obtained,
A3 representing the starting geometry in three dimensions in Cartesian and/or internal coordinates, and
B Ascertaining an optimized starting geometry by
B1 defining a function space encompassing the at least one bond from step A2 and the atoms joined by this bond,
B2 optimizing the geometry of the function space selected in step B1 by means of a quantum-chemical method and with a boundary condition that the length of the at least one bond selected in step A2 is kept constant, such that the optimized starting geometry is obtained,
B3 ascertaining a gradient norm B3 for the optimized starting geometry, by (i) determining a total energy of the optimized starting geometry as a function of the nuclear coordinates of the molecule in the optimized starting geometry, where the function is the quantum-chemical method of step B2, then (ii) determining the gradient norm B3 by calculating the Euclidean norm of the total energy of the optimized starting geometry as a first derivative thereof, and
B4.1 when the gradient norm B3 $\nabla$ is $0 \leq \nabla \leq 0.03$ $E_h$ $a_0^{-1}$, classifying the optimized starting geometry as a precursor to the transition state of the chemical reaction and continuing the method with step D1, or
B4.2 when the gradient norm B3 $\nabla$ is $>0.03$ $E_h$ $a_0^{-1}$, ascertaining the precursor to the transition state of the chemical reaction proceeding from the optimized starting geometry by a method comprising the following steps C:
C Ascertaining the precursor to the transition state of the chemical reaction by
C1 varying the optimized starting geometry using a Monte Carlo algorithm,
C1.1 wherein at least one atom from the function space selected in step B1 is selected at random,
C1.2 wherein a vector for a deflection of the atom chosen in step C1, and the magnitude for the vector, is selected at random, weighting the randomly selected magnitude of the vector by the gradient norm B3,
C1.3 wherein the atom selected in step C1.1 is deflected from the position of the atom in the optimized starting geometry using the vector from step C1.2, so as to obtain a precursor to the transition state of the chemical reaction,
C2 optimizing the geometry of the precursor to the transition state by means of the quantum-chemical method and with the boundary condition that the at least one bond from step A2 has the bond length that was ascertained in step C1.3,
C3 ascertaining the gradient norm C3 for the precursor to the transition state from step C2, by (i) determining a total energy of the precursor to the transition state as a function of the nuclear coordinates of the molecule in the precursor to the transition state, where the function is the quantum-chemical method of step C2, then (ii) determining the gradient norm C3 by calculating the Euclidean norm of the total energy of the optimized starting geometry as a first derivative thereof, and
C4.1 when the gradient norm C3 $\nabla$ is $0 \leq \nabla \leq 0.03$ $E_h$ $a_0^{-1}$, continuing the method with step D1, or
C4.2 when the gradient norm C3 $\nabla > 0.03$ $E_h$ $a_0^{-1}$, repeating steps C1 to C3 until a gradient norm C3 $\nabla$ of $0 \leq \nabla \leq 0.03$ $E_h$ $a_0^{-1}$ is obtained, wherein
(a) if steps C1 to C3 have been performed once, the geometry of the precursor to the transition state is varied in step C1 when the value of its gradient norm C3 is lower than the value of the gradient norm B3 of the optimized starting geometry, or
(b) if steps C1 to C3 have been performed more than once, the geometry of the optimized starting geometry or that precursor to the transition state from the preceding repetitions that has the lowest value for the gradient norm C3 or B3 compared to all the gradient norms C3 and B3 previously obtained is varied in step C1,
D Ascertaining the transition state by
D1 varying the precursor from step C4.1 or the precursor from step B4.1 by performing the following steps for one atom within the function space defined in B1:
D1.1 selecting an atom from the function space selected in step B1,
D1.2 selecting a vector for a deflection of the atom chosen in step D1.1,
D1.3 deflecting the atom selected in step D1.1 using the vector from step D1.2 from its position in the precursor, wherein the position is deflected once by the positive value of the magnitude of the vector and once by the negative value of the magnitude of the vector, such that two deflected precursors are obtained when steps D1.1 to D1.3 are conducted,
D2 optimizing the geometry of the two deflected precursors from step D1 by means of the quantum-chemical method under the constraint that the bond distances obtained in D1 are kept constant, such that two optimized precursors (i) and (ii) are obtained,
D3 calculating the energy of the two optimized precursors (i) and (ii) from step D2 by means of the quantum-chemical method,
D4 comparing the energy values of the two optimized precursors with the value of the gradient norm C3 or B3 of the precursor that was used in step D1,
D4.1 if the energy value of the optimized precursor (i) and the energy value of the optimized precursor (ii) are each smaller than the total energy of the precursor to the transition state determined in step C3, if the precursor from step C4.1 was used in step D1, or the total energy of the optimized starting geometry determined in step B3 if the precursor that was used in step D1, classifying the precursor from step B4.1 was used in step D1 as the transition state,
D4.2 if the energy value of the optimized precursor (i) or the energy value of the optimized precursor (ii) is not smaller than the total energy of the precursor to the transition state determined in step C3, if the precursor from step C4.1 was used in step D1, or the total energy of the optimized starting geometry determined in step B3 if the precursor from step B4.1 was used in step D1, repeating the method from step C1, and
E. selecting said catalyst and/or co-reactant in said chemical reaction based on the calculated transition state,
wherein $E_h$ is the Hartree energy, and
wherein $a_0^{-1}$ is the Bohr radius.

2. The method of claim 1, wherein the quantum-chemical method from steps B2, B3, C2, C3, D2 and D3 is a semiempirical method, density functional theory method or an approximation of the Schrödinger equation.

3. The method of claim 1, wherein the chemical reaction is a synthesis selected from the group consisting of polymer syntheses, syntheses of monomers for polymerization reactions, industrially required commodity chemicals, platform chemicals, additives, surfactants and active pharmacological ingredients.

4. The method of claim 1, wherein in step A1, at least two molecules I and II are provided and wherein in step A2, alternatively or additionally to the at least one bond, at least one distance between at least one atom from molecule I and at least one atom from molecule II and the length of the at least one distance is also selected, where the length of the distance is especially not more than 230 pm.

5. The method of claim 4, wherein molecule I is the catalyst for the chemical reaction, and molecule II is the co-reactant in the chemical reaction, and wherein molecule I has a size of 2 to 1000 atoms and molecule II has a size of 2 to 1000 atoms, where the sum total of the atoms from molecule I and from molecule II is especially to be more than 100 atoms.

6. The method of claim 5, wherein the molecule I is synthesized after step D.1 or after step D.2.

7. The method of claim 5, wherein after step D.1 or after step D.2, the chemical reaction is performed with molecule I as the catalyst.

8. The method of claim 5, wherein after step D.1 or after step D.2, the chemical reaction is performed with molecule II as the co-reactant.

9. The method of claim 1, wherein information as to the transition state ascertained in step D.1 or the optimized precursors ascertained in step D.2 is communicated to a user.

10. The method of claim 1, wherein information as to the transition state ascertained in step D.1 or the optimized precursors ascertained in step D.2 is received by a user.

\* \* \* \* \*